(12) United States Patent
Shuros et al.

(10) Patent No.: US 10,737,092 B2
(45) Date of Patent: Aug. 11, 2020

(54) DELIVERY DEVICES AND METHODS FOR LEADLESS CARDIAC DEVICES

(71) Applicant: CARDIAC PACEMAKERS, INC., St. Paul, MN (US)

(72) Inventors: Allan Charles Shuros, St. Paul, MN (US); Brian Soltis, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 233 days.

(21) Appl. No.: 15/939,745

(22) Filed: Mar. 29, 2018

(65) Prior Publication Data

US 2018/0280686 A1 Oct. 4, 2018

Related U.S. Application Data

(60) Provisional application No. 62/478,897, filed on Mar. 30, 2017.

(51) Int. Cl.
*A61N 1/05* (2006.01)
*A61N 1/375* (2006.01)

(52) U.S. Cl.
CPC .......... *A61N 1/057* (2013.01); *A61N 1/3756* (2013.01); *A61N 1/0573* (2013.01); *A61N 2001/058* (2013.01); *A61N 2001/0578* (2013.01)

(58) Field of Classification Search
CPC .. A61N 1/3756; A61N 1/37205; A61N 1/362; A61N 1/0573; A61N 2001/0578; A61N 2001/058; A61N 1/056; A61N 1/0587; A61N 1/059; A61N 1/057; A61N 1/3622; A61N 1/37512; A61B 17/3468; A61B 17/00234; A61B 2017/00243; A61B 2017/00331; A61M 25/0082; A61M 25/0147

See application file for complete search history.

(56) References Cited

U.S. PATENT DOCUMENTS

| 4,301,815 A | 11/1981 | Doring |
| 5,807,399 A | 9/1998 | Laske et al. |
| 5,908,381 A | 6/1999 | Aznoian et al. |

(Continued)

FOREIGN PATENT DOCUMENTS

| EP | 2818201 B1 | 7/2016 |
| EP | 2658599 B1 | 10/2016 |

(Continued)

*Primary Examiner* — Katherine M Shi
(74) *Attorney, Agent, or Firm* — Seager, Tufte & Wickhem LLP

(57) ABSTRACT

Delivery devices, systems, and methods for delivering implantable leadless pacing devices are disclosed. An example method for delivering the implantable leadless pacing device may include distally advancing an intermediate tubular member of a delivery system across the tricuspid valve and into the right ventricle. An outer tubular member of the delivery device may be torqued in a first direction to guide a distal holding section along the ventricular septum. The distal tip of the distal holding section may be releaseably secured to a tissue. After securing the distal tip of the distal holding section, the outer tubular member may be torqued in a second direction opposite to the first direction and the implantable leadless pacing device incrementally deployed.

11 Claims, 14 Drawing Sheets

(56) References Cited

U.S. PATENT DOCUMENTS

| | | |
|---|---|---|
| 6,181,973 B1 | 1/2001 | Ceron et al. |
| 6,224,725 B1 | 5/2001 | Glocker |
| 6,395,017 B1 | 5/2002 | Dwyer et al. |
| 6,409,674 B1 | 6/2002 | Brockway et al. |
| 6,497,803 B2 | 12/2002 | Glocker et al. |
| 6,551,477 B2 | 4/2003 | Glocker et al. |
| 6,582,441 B1 | 6/2003 | He et al. |
| 6,638,268 B2 | 10/2003 | Niazi |
| 6,786,918 B1 | 9/2004 | Krivoruchko et al. |
| 7,248,913 B2 | 7/2007 | Hassett |
| 7,321,798 B2 | 1/2008 | Muhlenberg et al. |
| 7,381,216 B2 | 6/2008 | Buzzard et al. |
| 7,499,758 B2 | 3/2009 | Cates et al. |
| 7,509,169 B2 | 3/2009 | Eigler et al. |
| 7,558,631 B2 | 7/2009 | Cowan et al. |
| 7,608,099 B2 | 10/2009 | Johnson et al. |
| 7,610,092 B2 | 10/2009 | Cowan et al. |
| 7,666,203 B2 | 2/2010 | Chanduszko et al. |
| 7,678,081 B2 | 3/2010 | Whiting et al. |
| 7,799,037 B1 | 9/2010 | He et al. |
| 7,840,281 B2 | 11/2010 | Kveen et al. |
| 7,937,161 B2 | 5/2011 | Hastings et al. |
| 7,993,351 B2 | 8/2011 | Worley et al. |
| 7,996,087 B2 | 8/2011 | Cowan et al. |
| 8,002,822 B2 | 8/2011 | Glocker et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,315,701 B2 | 11/2012 | Cowan et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,398,610 B2 | 3/2013 | Locsin et al. |
| 8,428,750 B2 | 4/2013 | Kolberg |
| 8,433,402 B2 | 4/2013 | Ruben et al. |
| 8,478,431 B2 | 7/2013 | Griswold et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,615,310 B2 | 12/2013 | Khairkhahan et al. |
| 8,634,912 B2 | 1/2014 | Bornzin et al. |
| 8,634,919 B1 | 1/2014 | Hou et al. |
| 8,670,842 B1 | 3/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,831,741 B2 | 9/2014 | Griswold |
| 8,855,789 B2 | 10/2014 | Jacobson |
| 8,894,824 B2 | 11/2014 | Glocker et al. |
| 8,903,513 B2 | 12/2014 | Ollivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 9,008,776 B2 | 4/2015 | Cowan et al. |
| 9,020,611 B2 | 4/2015 | Khairkhahan et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,138,583 B2 | 9/2015 | Holmstrom et al. |
| 9,155,882 B2 | 10/2015 | Grubac et al. |
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |
| 9,272,155 B2 | 3/2016 | Ostroff |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,351,648 B2 | 5/2016 | Mothilal et al. |
| 9,358,387 B2 | 6/2016 | Suwito et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bornzin et al. |
| 9,468,773 B1 | 10/2016 | Anderson et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,610,454 B2 | 4/2017 | Doan et al. |
| 9,623,234 B2 | 4/2017 | Anderson |
| 9,662,487 B2 | 5/2017 | Kveen et al. |
| 9,675,798 B2 | 6/2017 | Grubac et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 2003/0078618 A1 | 4/2003 | Fey et al. |
| 2005/0101984 A1 | 5/2005 | Chanduszko et al. |
| 2005/0165472 A1 | 7/2005 | Glocker |
| 2005/0209653 A1 | 9/2005 | Herbert et al. |
| 2005/0267555 A1 | 12/2005 | Marnfeldt et al. |
| 2006/0009737 A1 | 1/2006 | Whiting et al. |
| 2006/0106442 A1 | 5/2006 | Richardson et al. |
| 2006/0136004 A1 | 6/2006 | Cowan et al. |
| 2007/0078490 A1 | 4/2007 | Cowan et al. |
| 2009/0082828 A1 | 3/2009 | Ostroff |
| 2010/0030061 A1 | 2/2010 | Canfield et al. |
| 2010/0063562 A1 | 3/2010 | Cowan et al. |
| 2010/0228308 A1 | 9/2010 | Cowan et al. |
| 2010/0274227 A1 | 10/2010 | Khairkhahan et al. |
| 2011/0112548 A1 | 5/2011 | Fifer et al. |
| 2011/0251589 A1 | 10/2011 | Locsin et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2012/0095539 A1 | 4/2012 | Khairkhahan et al. |
| 2012/0109148 A1 | 5/2012 | Bonner et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0232565 A1 | 9/2012 | Kveen et al. |
| 2012/0239002 A1 | 9/2012 | Griswold |
| 2013/0012925 A1 | 1/2013 | Berthiaume et al. |
| 2013/0035636 A1 | 2/2013 | Beasley et al. |
| 2013/0053915 A1 | 2/2013 | Holmstrom et al. |
| 2013/0103047 A1 | 4/2013 | Steingisser et al. |
| 2013/0123872 A1 | 5/2013 | Bornzin et al. |
| 2013/0131591 A1* | 5/2013 | Berthiaume ......... A61N 1/3756 604/95.04 |
| 2013/0253342 A1 | 9/2013 | Griswold et al. |
| 2013/0253346 A1 | 9/2013 | Griswold et al. |
| 2013/0282073 A1 | 10/2013 | Cowan et al. |

(56) References Cited

U.S. PATENT DOCUMENTS

| | | |
|---|---|---|
| 2014/0018818 A1 | 1/2014 | Somogyi et al. |
| 2014/0257324 A1 | 9/2014 | Fain |
| 2014/0324145 A1 | 10/2014 | Eggen et al. |
| 2014/0378991 A1 | 12/2014 | Ollivier |
| 2015/0039070 A1 | 2/2015 | Kuhn et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0088155 A1 | 3/2015 | Stahmann et al. |
| 2015/0094668 A1 | 4/2015 | Wood et al. |
| 2015/0094735 A1 | 4/2015 | Ward et al. |
| 2015/0238768 A1 | 8/2015 | Bornzin |
| 2015/0283376 A1 | 10/2015 | Ollivier et al. |
| 2015/0306378 A1 | 10/2015 | Schmidt et al. |
| 2015/0306381 A1 | 10/2015 | Schmidt et al. |
| 2015/0328459 A1 | 11/2015 | Chin et al. |
| 2015/0335884 A1 | 11/2015 | Khairkhahan et al. |
| 2015/0352351 A1 | 12/2015 | Muessig et al. |
| 2015/0352365 A1 | 12/2015 | Holmstrom et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0114156 A1 | 4/2016 | Haasl et al. |
| 2016/0114157 A1 | 4/2016 | Haasl et al. |
| 2016/0158560 A1 | 6/2016 | Moore et al. |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |

FOREIGN PATENT DOCUMENTS

| | | |
|---|---|---|
| EP | 2651502 B1 | 11/2016 |
| EP | 2771064 B1 | 1/2017 |
| EP | 2780077 B1 | 1/2017 |

\* cited by examiner

DELIVERY DEVICES AND METHODS FOR LEADLESS CARDIAC DEVICES

CROSS REFERENCE TO RELATED APPLICATIONS

The present application claims the benefit of and priority to U.S. Provisional Patent Application Ser. No. 62/478,897, filed Mar. 30, 2017, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, a delivery device for delivering an implantable leadless pacing device may comprise an outer tubular member including a lumen extending from a proximal end to a distal end thereof, the outer tubular member may be configured to be deflectable in a first a plane, an intermediate tubular member including a lumen extending from a proximal end to a distal end thereof, the intermediate tubular member may be slidably disposed within the lumen of the outer tubular member, the intermediate tubular member may include a distal holding section defining a cavity therein for receiving an implantable leadless pacing device, and the intermediate tubular member may be configured to be deflectable in a second plane different from the first plane. The delivery device may further comprise an inner tubular member including a lumen extending from a proximal end to a distal end thereof, the inner tubular member may be slidably disposed within the lumen of the intermediate tubular member, a handle assembly including at least a first hub portion may be affixed adjacent to the proximal end of the outer tubular member, a second hub portion may be affixed adjacent to the proximal end of the intermediate tubular member, and a third hub portion may be affixed adjacent to the proximal end of the inner tubular member and a first actuation mechanism may be positioned at the handle assembly and configured to deflect the outer tubular member.

Alternatively or additionally to any of the examples above, in another example, the intermediate tubular member may be deflectable about a fixed curve along a portion of a length of the intermediate tubular member.

Alternatively or additionally to any of the examples above, in another example, the fixed curve may include one or more nitinol wires embedded in a body of the intermediate tubular member.

Alternatively or additionally to any of the examples above, in another example, the delivery device may further comprise a second actuation mechanism positioned at the handle assembly and may be configured to deflect the intermediate tubular member.

Alternatively or additionally to any of the examples above, in another example, the delivery device may further comprise an active anchor element positioned adjacent to the distal holding section.

Alternatively or additionally to any of the examples above, in another example, the active anchor element may be configured to be actuated between a retracted delivery configuration and an extended fixation configuration.

Alternatively or additionally to any of the examples above, in another example, the active anchor element may be positioned along an outer surface of the distal holding section.

Alternatively or additionally to any of the examples above, in another example, the active anchor element may be positioned within the cavity of the distal holding section.

Alternatively or additionally to any of the examples above, in another example, the active anchor element may comprise a wire having an atraumatic distal tip.

Alternatively or additionally to any of the examples above, in another example, the active anchor element may be configured to engage a tissue to temporarily fixate the distal holding section to the tissue.

Alternatively or additionally to any of the examples above, in another example, a counter-clockwise torquing motion on the outer tubular member may be configured to direct an opening of the cavity towards a septal wall of a heart.

In another example, a method of separately actuating an outer tubular member affixed to a first hub portion, an intermediate tubular member affixed to a second hub portion, and an inner tubular member affixed to a third hub portion of a delivery device may comprise rotating the first hub portion in a first direction, fixating a distal end portion of the intermediate tubular portion, and after fixating the distal end portion of the intermediate tubular member to a septal wall of a heart, rotating the first hub portion in a second direction opposite the first direction.

Alternatively or additionally to any of the examples above, in another example, prior to rotating the first hub portion in the first direction, the second hub portion may be distally advanced.

Alternatively or additionally to any of the examples above, in another example, the outer tubular member may be deflectable in a first plane.

Alternatively or additionally to any of the examples above, in another example, the intermediate tubular member may be deflectable in a second plane different from the first plane.

In another example, a method of delivering an implantable leadless pacing device to a ventricular septum may comprise advancing a delivery device through the vasculature and into the right atrium. The delivery device may comprise an outer tubular member including a lumen extending from a proximal end to a distal end thereof, the outer tubular member configured to be deflectable in a first a plane, an intermediate tubular member including a lumen extending from a proximal end to a distal end thereof, the intermediate tubular member slidably disposed within the lumen of the outer tubular member, the intermediate tubular member including a distal holding section defining a cavity therein for receiving an implantable leadless pacing device, and the intermediate tubular member configured to be deflectable in a second plane different from the first plane, an inner tubular member including a lumen extending from a proximal end to a distal end thereof, the inner tubular member slidably disposed within the lumen of the intermediate tubular member, a handle assembly including at least a first hub portion affixed adjacent to the proximal end of the outer tubular member, a second hub portion affixed adjacent to the proximal end of the intermediate tubular member, and a third hub portion affixed adjacent to the proximal end of the inner tubular member; and a first actuation mechanism positioned at the handle assembly and configured to deflect the outer tubular member. The method may further comprise distally advancing the intermediate tubular member across the tricuspid valve and into the right ventricle, torqueing the outer tubular member in a first direction to guide the distal holding section along the ventricular septum, releaseably securing a distal tip of the distal holding section to a tissue in the ventricular septum, after securing the distal tip of the distal holding section, torquing the outer tubular member in a second direction opposite to the first direction, and incrementally deploying an implantable leadless pacing device.

Alternatively or additionally to any of the examples above, in another example, the implantable leadless pacing device may be deployed such that a longitudinal axis of the implantable leadless pacing device is at an angle of in the range of 5 to 45° to the ventricular septum.

Alternatively or additionally to any of the examples above, in another example, releaseably securing the distal tip of the distal holding section to the tissue may comprise a passive anchoring of the distal tip to the ventricular septum.

Alternatively or additionally to any of the examples above, in another example, releaseably securing the distal tip of the distal holding section to the tissue may comprise an active anchoring of an active anchoring element to the ventricular septum.

Alternatively or additionally to any of the examples above, in another example, the method may further comprise unsecuring the distal tip of the distal holding section from the tissue after the implantable leadless pacing device has been at least partially deployed.

Alternatively or additionally to any of the examples above, in another example, torqueing the outer tubular member in the first direction may comprise deflecting the outer tubular member in the first plane.

Alternatively or additionally to any of the examples above, in another example, torquing the outer tubular member in the second direction opposite to the first direction may orient an opening of the distal holding section towards the ventricular septum.

In another example, a delivery device for delivering an implantable leadless pacing device may comprise an outer tubular member including a lumen extending from a proximal end to a distal end thereof, the outer tubular member configured to be deflectable in a first a plane, an intermediate tubular member including a lumen extending from a proximal end to a distal end thereof, the intermediate tubular member slidably disposed within the lumen of the outer tubular member, the intermediate tubular member including a distal holding section defining a cavity therein for receiving an implantable leadless pacing device, and the intermediate tubular member configured to be deflectable in a second plane different from the first plane, an inner tubular member including a lumen extending from a proximal end to a distal end thereof, the inner tubular member slidably disposed within the lumen of the intermediate tubular member, a handle assembly including at least a first hub portion affixed adjacent to the proximal end of the outer tubular member, a second hub portion affixed adjacent to the proximal end of the intermediate tubular member, and a third hub portion affixed adjacent to the proximal end of the inner tubular member, and a first actuation mechanism positioned at the handle assembly and configured to deflect the outer tubular member.

Alternatively or additionally to any of the examples above, in another example, the intermediate tubular member may be deflectable about a fixed curve along a portion of a length of the intermediate tubular member.

Alternatively or additionally to any of the examples above, in another example, the fixed curve may include one or more nitinol wires embedded in a body of the intermediate tubular member.

Alternatively or additionally to any of the examples above, in another example, the delivery device may further comprise a second actuation mechanism positioned at the handle assembly and configured to deflect the intermediate tubular member.

Alternatively or additionally to any of the examples above, in another example, the delivery device may further comprise an active anchor element positioned adjacent to the distal holding section.

Alternatively or additionally to any of the examples above, in another example, the active anchor element may be configured to be actuated between a retracted delivery configuration and an extended fixation configuration.

Alternatively or additionally to any of the examples above, in another example, the active anchor element may comprise a wire having an atraumatic distal tip.

Alternatively or additionally to any of the examples above, in another example, the active anchor element may be configured to engage a tissue to temporarily fixate the distal holding section to the tissue.

Alternatively or additionally to any of the examples above, in another example, a counter-clockwise torquing motion on the outer tubular member may be configured to direct an opening of the cavity towards a target region.

In another example, a method of separately actuating an outer tubular member affixed to a first hub portion, an intermediate tubular member affixed to a second hub portion, and an inner tubular member affixed to a third hub portion of a delivery device may comprise rotating the first hub portion in a first direction, fixating a distal end portion of the intermediate tubular portion to a ventricular septum, and after fixating the distal end portion of the intermediate tubular member, rotating the first hub portion in a second direction opposite the first direction.

Alternatively or additionally to any of the examples above, in another example, prior to rotating the first hub portion in the first direction, the second hub portion may be distally advanced.

Alternatively or additionally to any of the examples above, in another example, the outer tubular member may be deflectable in a first plane Alternatively or additionally to any of the examples above, in another example, the intermediate tubular member may be deflectable in a second plane different from the first plane.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
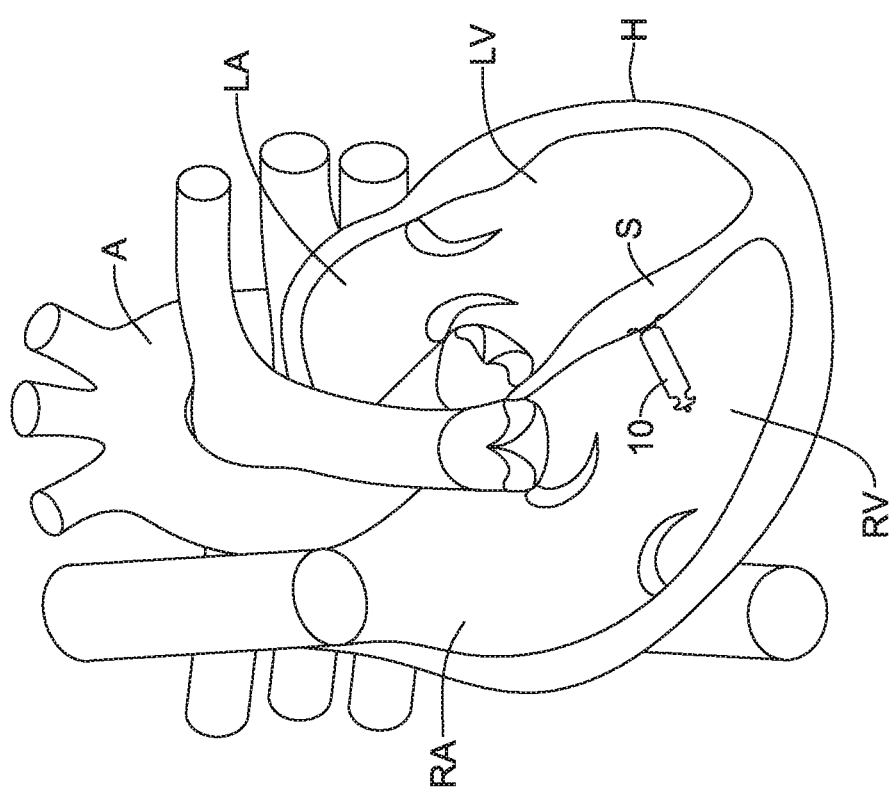
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. In some cases, it may be desirable to deliver the capsule to the ventricular septum to reduce the risk of the device perforating a chamber free wall. Accordingly, it may be desirable to provide delivery devices which facilitate advancement through the vasculature and into the heart to allow for delivery and placement to the ventricular septum.

FIG. 1 illustrates an example implantable leadless cardiac pacing device 10 (e.g., a leadless pacemaker) implanted in a chamber of a heart H, such as the right ventricle RV. In some cases, the device 10 may be affixed to the ventricular septum S, as shown. The right atrium RA, left atrium LA, left ventricle LV, and aorta A are also illustrated. Although shown implanted in the right ventricle RV, it is contemplated that the implantable device 10 may alternatively be implanted in the right atrium RA, left atrium LA, left ventricle LV, or other cardiovascular location, if desired.

Figure 2:
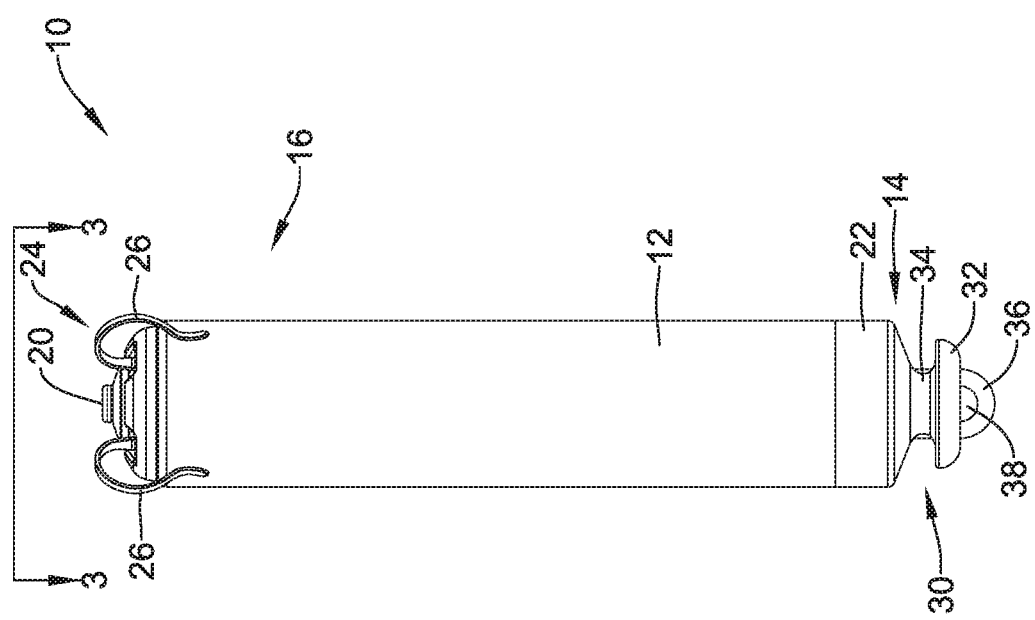
FIG. 2 is a side view of an example implantable leadless cardiac pacing device.
Figure 3:
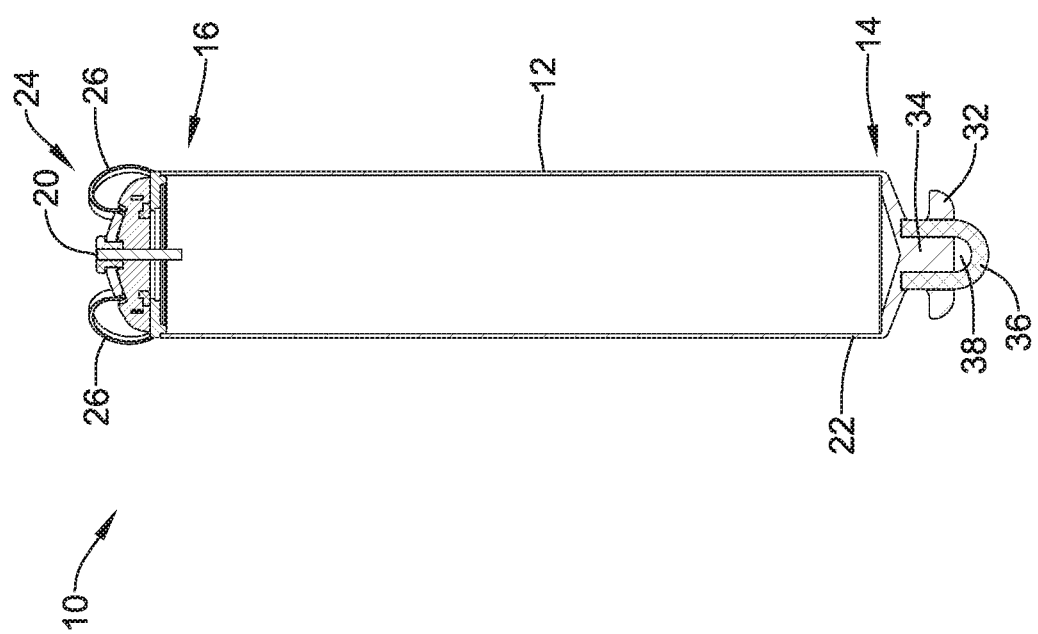
FIG. 3 is a cross-sectional view of the implantable leadless cardiac pacing device of FIG. 2.

A side view of the illustrative implantable device 10 is shown in FIG. 2 and a cross-sectional view of the illustrative implantable device 10, taken at line 3-3 in FIG. 2, is illustrated in FIG. 3. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery)

within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks or tines 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g., looped) through the opening 38. The retention structure 36 may extend through the head portion 32, along the neck portion 34, and to or into the proximal end 14 of the housing 12, as is shown more clearly in FIG. 3. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, the ventricular septum. The target region may also include other regions of the heart (e.g., a portion of the right ventricle near the apex of the heart, right atrium, left atrium, or left ventricle), blood vessels, or other suitable targets. It may be desirable to provide the delivery system with certain features that may allow for easier or better control for navigation or delivery purposes.

Current delivery strategies may include delivering the device 10 to the apical septum where the heart wall is thicker than, for example, a free wall. In such an instance, the delivery catheter may be dependent on a structure within the heart for the tip of the delivery system to rest upon. This may limit the flexibility of the system and as well as limit the ability to direct the distal end of the delivery system towards a portion of the ventricular septum that may be thicker than, for example, the apical septum and/or a free wall. Further, it may be difficult for the relatively long delivery system to steer the distal end such that it approaches the ventricular septum at an angle instead of parallel to the long axis of the ventricle. It may be desirable to provide a delivery system and delivery methods which allow the distal end of the delivery device to be oriented at more of an angle to the right ventricular septum such that the device 10 can be deployed in the ventricular septum, in the thicker region thereof. Some illustrative delivery devices may be found in commonly assigned US Patent Publication No. 2016/0114156, titled DELIVERY DEVICES AND METHODS FOR LEADLESS CARDIAC DEVICES, US Patent Publication No. 2016/0114157, titled DELIVERY DEVICES AND METHODS FOR LEADLESS CARDIAC DEVICES, and U.S. patent application Ser. No. 15/354,432 filed on Nov. 17, 2016, titled DELIVERY DEVICES AND METHODS FOR LEADLESS CARDIAC DEVICES, the disclosures of which are incorporated herein by reference.

Figure 4:
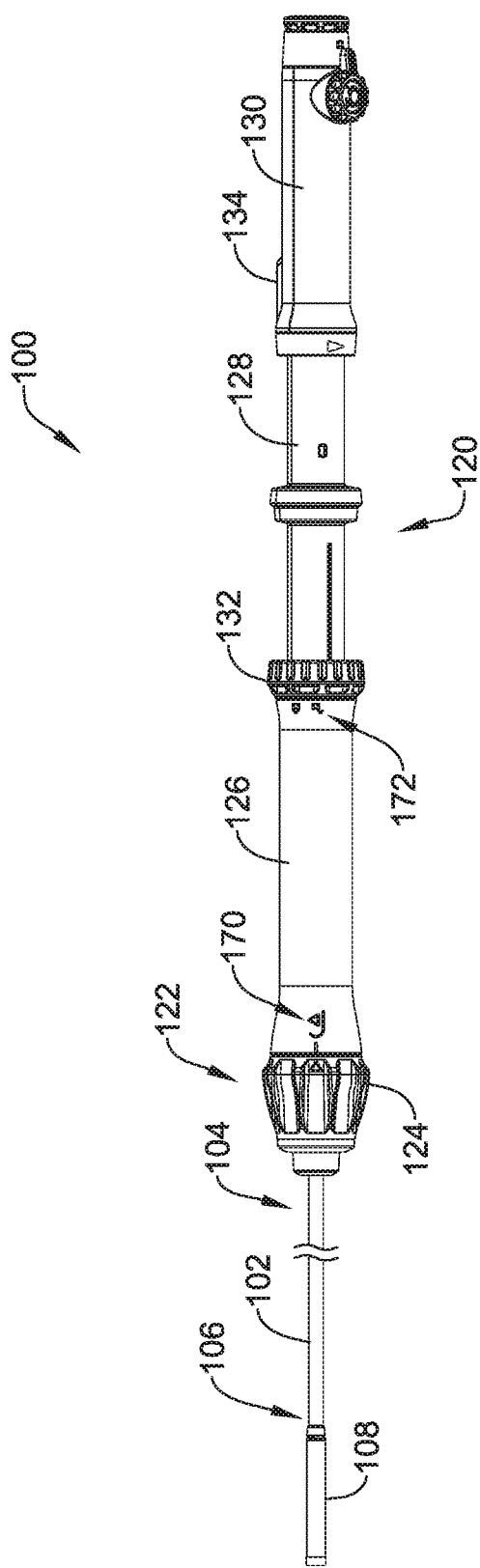
FIG. 4 is a plan view of an example delivery device for an implantable leadless cardiac pacing device.

FIG. 4 is a plan view of an illustrative delivery device 100, such as a catheter, that may be used to deliver the implantable device 10. The delivery device 100 may include an outer tubular member 102 having a proximal section 104 and a distal section 106. An intermediate tubular member 110 may be longitudinally slidably disposed within a lumen 150 of the outer tubular member 102 (see e.g., FIG. 5). An inner tubular member 116 may be longitudinally slidably disposed within a lumen 152 of the intermediate tubular member 110 (see e.g., FIG. 5). A distal holding section 108 may be attached to a distal end portion 114 of the intermediate tubular member 110. The delivery device 100 may also include a handle assembly 120 positioned adjacent to the proximal section 104 of the outer tubular member 102. In some embodiments, the outer tubular member 102 may include at least a section thereof that has an outer diameter D2 that is less than the outer diameter D1 of at least a portion of the holding section 108 (see e.g., FIG. 5).

Figure 5:
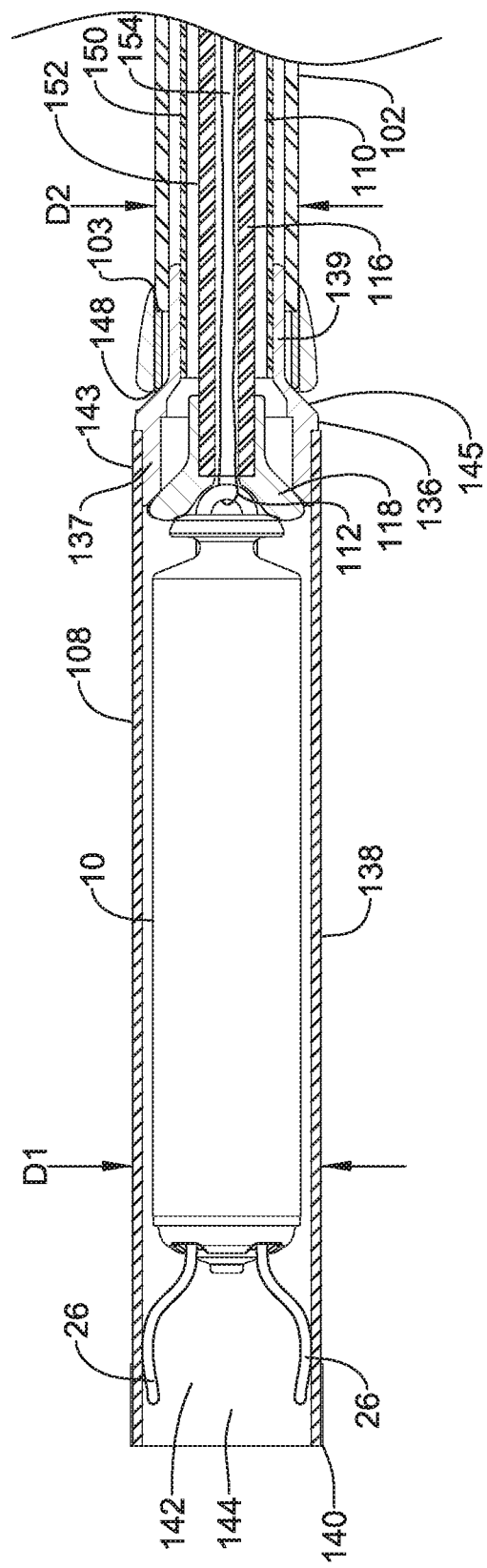
FIG. 5 is a partial cross-sectional side view of the distal portion of the delivery device of FIG. 4.

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g., FIG. 5). The first hub portion 126, second hub portion 128, and third hub portion 130 may be positioned in a generally telescoping arrangement and longitudinally slidable relative to each other. Each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously.

The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the intermediate tubular member 110.

The distal holding section 108 may be configured to receive the implantable device 10 therein. For example, referring to FIG. 5, which illustrates a cross-sectional view of a distal portion of the delivery device 100, the holding section 108 may define a cavity 142 for slidably receiving the implantable device 10, and may include a distal opening 144 for slidable insertion and/or extraction of the implantable device 10 into and/or out of the cavity 142.

The distal holding section 108 may include a body portion 138 and a distal tip portion 140 that may be, for example, configured to be atraumatic to anatomy, such as a bumper tip. For example, as the catheter is navigated through the anatomy, the distal tip 140 may come into contact with anatomy. Additionally, when the catheter is used to deliver the device, the tip 140 of the delivery device 100 will likely come into contact with tissue adjacent the target site (e.g., cardiac tissue of the heart). A hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma.

For example, the distal tip 140 may be made of a material that is softer than the body portion 138 of the distal holding section 108. In some cases, the distal tip 140 may include a material that has a durometer that is less than the durometer of the material of the body portion 138. In some particular embodiments, the durometer of the material used in the distal tip 140 may be in the range of about 5 Shore D to about 70 Shore D, or for example, in the range of about 25 Shore D to about 65 Shore D. Additionally, the distal tip 140 may include a shape or structure that may make it less traumatic to tissue. For example, the distal tip 140 may have a distal surface, such as a tissue contacting surface, that is that is rounded or includes a curvature configured to be more atraumatic to tissue.

In some embodiments, all or a portion of the distal holding section 108 may include an inner surface that may be configured to resist getting caught on the fixation mechanism 24, such as the one or more, or a plurality of hooks or tines 26 on the device 10. For example, the distal holding section 108 may include an inner layer or coating of harder or more lubricious material that resists force applied by the fixation mechanism 24 onto the inner surface of the distal holding section 108. For example, the distal holding section 108 may include a multi-layered structure, and an inner layer may be made of a material that is harder than an outer layer.

The inner tubular member 116 may be disposed (e.g., slidably disposed) within a lumen 152 of the intermediate tubular member 110. The inner tubular member 116 may be engaged by a user near or at the third hub portion 130, and extend through a lumen 152 of the intermediate tubular member 110 and into the distal holding section 108. A distal portion 118 of the inner tubular member 116 may be capable of engaging the device 10, and the inner tubular member 116 may be used to "push" the device 10 out from distal holding section 108 so as to deploy and anchor device 10 within a target region (e.g., a region of the heart such as the right ventricle). The inner tubular member 116 may have a lumen 154 extending from the proximal end 117 to a distal portion 118 thereof. A tether 112 or other retaining feature may be used to releasably secure the device 10 to the delivery device 100. In some instances, the tether 112 may be a single or unitary length of material that may extend from a proximal end 117 of the lumen 154, out through the distal portion 118, through the opening 38 of the device 10 and return to the proximal end 117 of the inner tubular member 116 through the lumen 154 such that both ends of the tether 112 are positioned adjacent to the third hub portion 130. In some instances, the ends of the tether 112 may be secured within a locking feature in the third hub portion 130.

In order to more specifically place or steer the delivery device 100 to a position adjacent to the intended target, the delivery device 100 may be configured to be deflectable or articulable or steerable. Referring to FIG. 4, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the holding section 108 is in a desirable position or orientation for navigation or delivery of the device 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material(s) and mechanism(s) may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the outer tubular member 102 to be predisposed to be bent and/or deflected in a certain direction or configuration when compression and/or tension forces are applied thereto. It is contemplated that the outer tubular member 102 may be a laser cut metallic tubing, a braid reinforced polymeric tubing, or other flexible tubular structure as desired.

Returning again to FIG. 5, the distal holding section 108 may be affixed to a distal end portion 114 of the intermediate tubular member 110. The distal holding section 108 may include a hub portion 136 and a tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some embodiments, the outer tubular member 102 may include a metal ring or tip adjacent the distal end 103 thereof for attaching one or more pull wires thereto. It is contemplated that the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. It is contemplated that the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surface may engage as the proximal end portion 139 is proximally retracted within the outer tubular member 102. Other coupling arrangements may be used as desired.

It is contemplated that as the outer tubular member 102 is bent to navigate the implantable device 10 to the desired location, the proximal end portion 139 may advance distally and disengage from the inner surface of the outer tubular member 102 creating a kink point or weakened region adjacent to the bonding region 146. Proximally retracting the intermediate tubular member 110 to bring the intermediate region 145 into contact with the outer tubular member 102 at contact point 148 and/or bringing the proximal end portion 139 into the outer tubular member 102 and fixing the intermediate tubular member 110 in this configuration may help prevent migration of the distal holding section 108 during navigation of the delivery device 100 to the desired location. Such a configuration may also place the intermediate tubular member 110 in tension while the distal holding section 108 applies a compression force on the outer tubular member 102, as will be discussed in more detail below. As discussed above, a locking mechanism 132 in the handle assembly 120 may be utilized to releasably maintain the outer tubular member 102 and the intermediate tubular member 110 in a desired orientation.

Figure 6A:
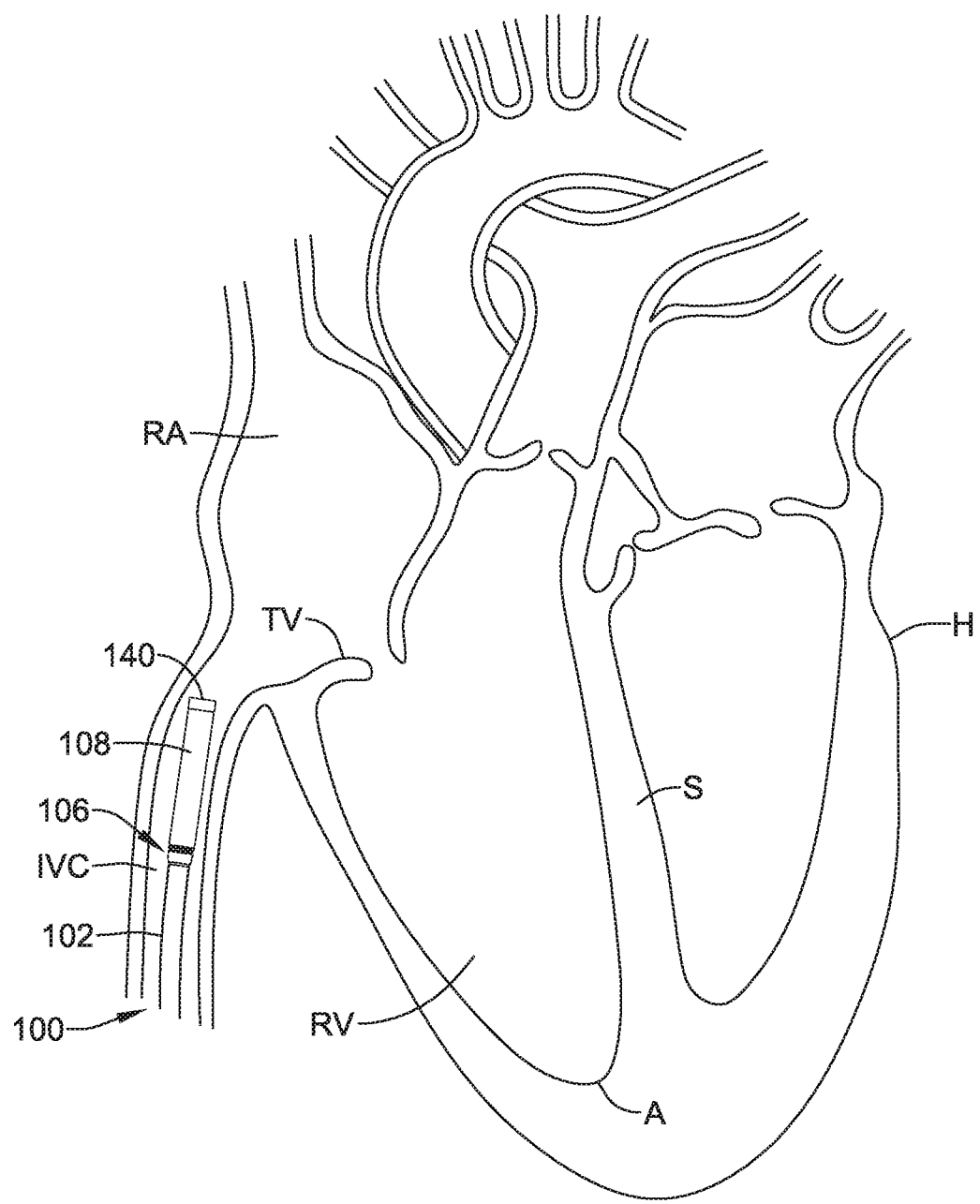
FIGS. 6A-6G are schematic views illustrating the use of the illustrative delivery device to deploy an implantable leadless cardiac pacing device.

Referring now to FIGS. 6A-6G, an exemplary method for deploying a device 10 to, for example, the ventricular septum S using the illustrative delivery device 100 will now be described with respect to the distal section and distal holding section 108. The delivery device 100 may be introduced into the vasculature through the femoral vein through a previously introduced sheath catheter (not explicitly shown). The delivery device 100 may be introduced through any desired location and with or without the use of an introducer sheath as desired. The delivery device 100 may be advanced through the vasculature to the desired treatment location, which, in the case of a leadless cardiac pacing device, may be a chamber of the heart H. For example, the delivery device 100 may be advanced through the vasculature to the inferior vena cava IVC, as shown in FIG. 6A, and into the right atrium RA. The clinician may use the actuation mechanism 122 to deflect the distal end portion 106 of the outer tubular member 102 in a desired manner to facilitate advancement and/or placement of the delivery device 100. During advancement of the delivery device 100, the handle assembly 120 may be in a fully extended configuration. In such a configuration, the third hub portion 130 may be at its proximal-most location relative to the second hub portion 128 and the first hub portion 126 may be at its distal-most location relative to the second hub portion 128. When the handle assembly 120 is in its fully extended configuration, the inner tubular member 116, intermediate tubular member 110, and the outer tubular member 102 may be oriented in the manner illustrated in FIG. 5. The delivery device 100 can be imaged using known techniques to ensure accurate placement of the device 10.

Figure 6B:
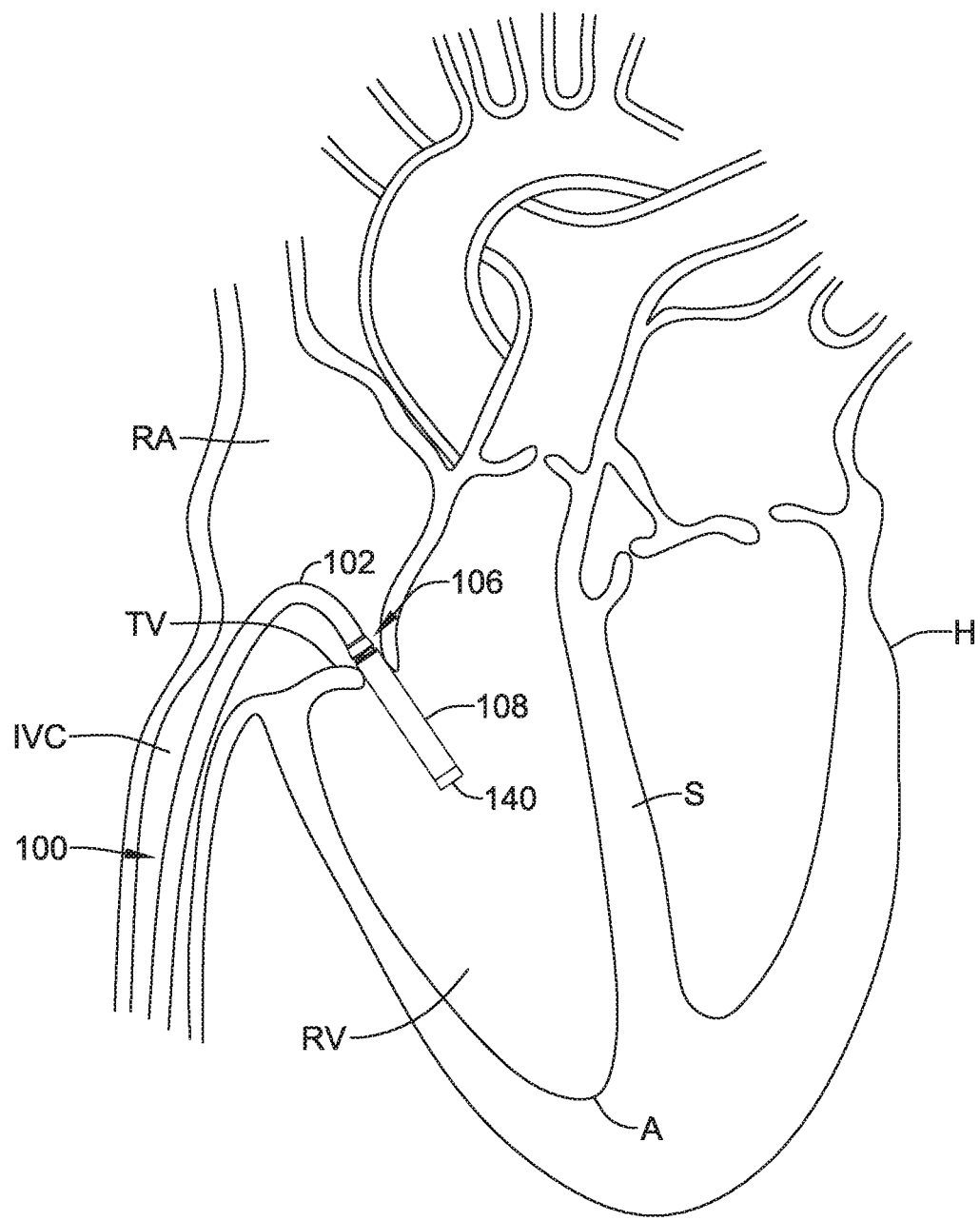

As the distal tip portion 140 of the distal holding section 108 enters the junction of the inferior vena cava IVC and the right atrium RA, the clinician may begin to deflect the outer tubular member 102 (and/or intermediate tubular member 110), as described above with respect to FIG. 4. It is contemplated that the outer tubular member 102 may be capable of deflection angles of up 180°, or more. The clinician may use a combination of skillful catheter manipulation (e.g. sweeping, rotating, etc.) and deflection to locate the tricuspid valve TV. Once the tricuspid valve TV has been located, the clinician may further advance and/or deflect the delivery device 100 to advance the distal holding section 108 into the right ventricle RV, as shown in FIG. 6B. In some instances, deflection of the outer tubular member 102 may be sufficient to move the distal tip portion 140 across the tricuspid valve TV and into the right ventricle RV. In other instances, the outer tubular member 102 may first be deflected and then the delivery device 100 pushed across the tricuspid valve TV.

Once the distal holding section 108 has been advanced across the tricuspid valve TV and into the right ventricle RV, the clinician may advance the distal holding section 108 and the intermediate tubular member 110 without advancing the outer tubular member 102 (i.e., telescoping the intermediate tubular member 110). It is contemplated that the entire distal holding section 108 need not be in the right ventricle RV to begin advancing the distal holding section 108 and the intermediate tubular member 110 without advancing the outer tubular member 102. For example, in some instances only a portion of the length of the distal holding section 108 may be in the right ventricle RV prior to telescoping the distal holding section 108 from the outer tubular member 102. It is contemplated that, in some instances, less than one-third or less than one-half of the distal holding section 108 may be positioned in the right ventricle RV when the intermediate tubular member 110 is telescoped distal of the distal end of the outer tubular member 102. In other instances, the entire length or substantially the entire length of the distal holding section 108 may be positioned in the right ventricle RV when the intermediate tubular member 110 is telescoped distal of the distal end of the outer tubular member 102. An average heart may have an average distance of approximately 7.5 centimeters between the tricuspid valve TV and an apex A of the right ventricle RV. In some instances, the distance between the tricuspid valve TV and the apex A of the right ventricle RV may be in the range of 4 to 12 centimeters or in the range of 6 to 10 centimeters. In a smaller heart, it may be possible for a portion of the distal holding section 108 to remain in the right atrium RA while in a larger heart the distal holding section 108 may need to be fully advanced into the right ventricle RV. For example, the distal holding portion 108 may have a length in the range of 3.5 to 5.5 centimeters or in the range of 4.0 to 5.0 centimeters. In some instances, the delivery device 100 may have a telescoping distance in the range of 3 to 10 centimeters or the in the range of 4 to 7 centimeters, for example.

Figure 6C:
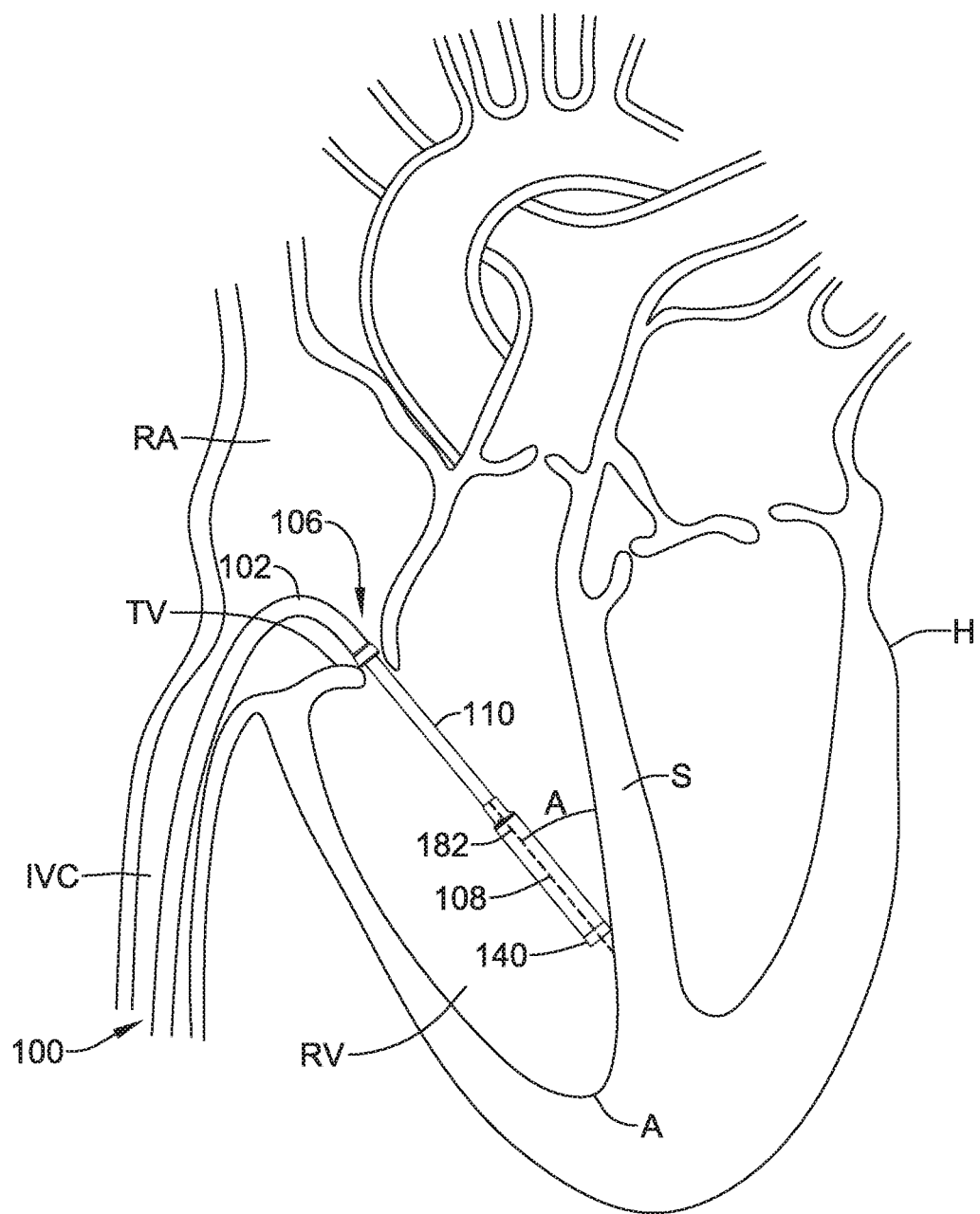

Once the distal holding section 108 has been advanced, partially or fully, into the right ventricle, the handle assembly 120 (e.g., the first hub portion 126) may be torqued or rotated in a first direction (for example, in the clockwise direction) such that the distal holding section 108 is along the septum S, as shown in FIG. 6C. While the intermediate tubular member 110 is shown in an extended or telescoped configuration, it is contemplated that the distal holding section 108 may be guided or positioned along the septum S with or without telescoping the intermediate tubular member 110.

The distal holding section 108 and the intermediate tubular member 110 may be advanced until the distal tip portion 140 of the distal holding section 108 contacts the ventricular septum S of the heart H, as shown in FIG. 6C. In some cases, a longitudinal axis 182 of the distal holding section 108 may be generally parallel to the septum S. For example, the longitudinal axis 182 of the distal holding section 108 may be considered generally parallel to the septum S when the longitudinal axis 182 of the distal holding section 108 is oriented at an angle A of 10° or less relative to the septum S. In other cases, the longitudinal axis 182 of the distal holding section 108 may be at any angle A between 0° (e.g., parallel to the septum S) and 90°, between 5° and 80°, between 5° and 75°, between 5° and 60°, or between 5° and 45° to the septum S. In some instances, a portion of the distal tip portion 140 may be placed in contact with the septum S of the right ventricle RV. In some instances, the location of the distal tip portion 140 may be confirmed with contrast media and imaging. For example, contrast confirmation may be used to confirm the distal tip portion 140 is engaged with a wall of the heart H prior to deploying the implantable device 10. It is further contemplated that the intermediate tubular member 110 may be formed from a flexible material, such as, but not limited to a 35 D durometer polyether block amide (PEBA, for example available under the trade name PEBAX®). It is contemplated that a flexible material may buckle or flex with an applied force (e.g. from the clinician) when the distal tip portion 140 is in contact with the wall of the heart H. This may provide additional confirmation under imaging that the distal tip portion 140 is engaged with the wall of the heart H. It is further contemplated that a flexible intermediate tubular member 110 may facilitate navigation of the delivery device 100.

Figure 6D:
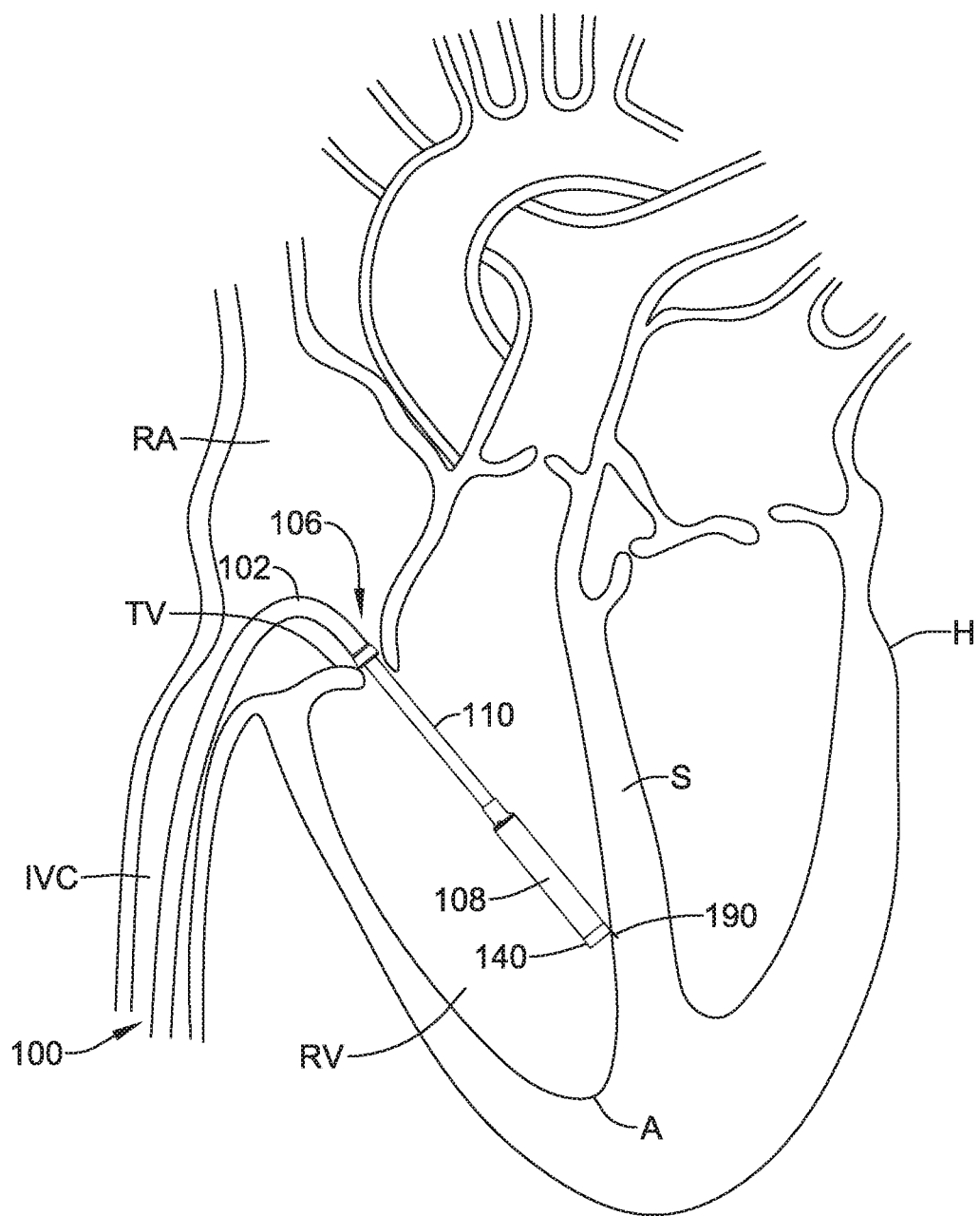
Figure 7:
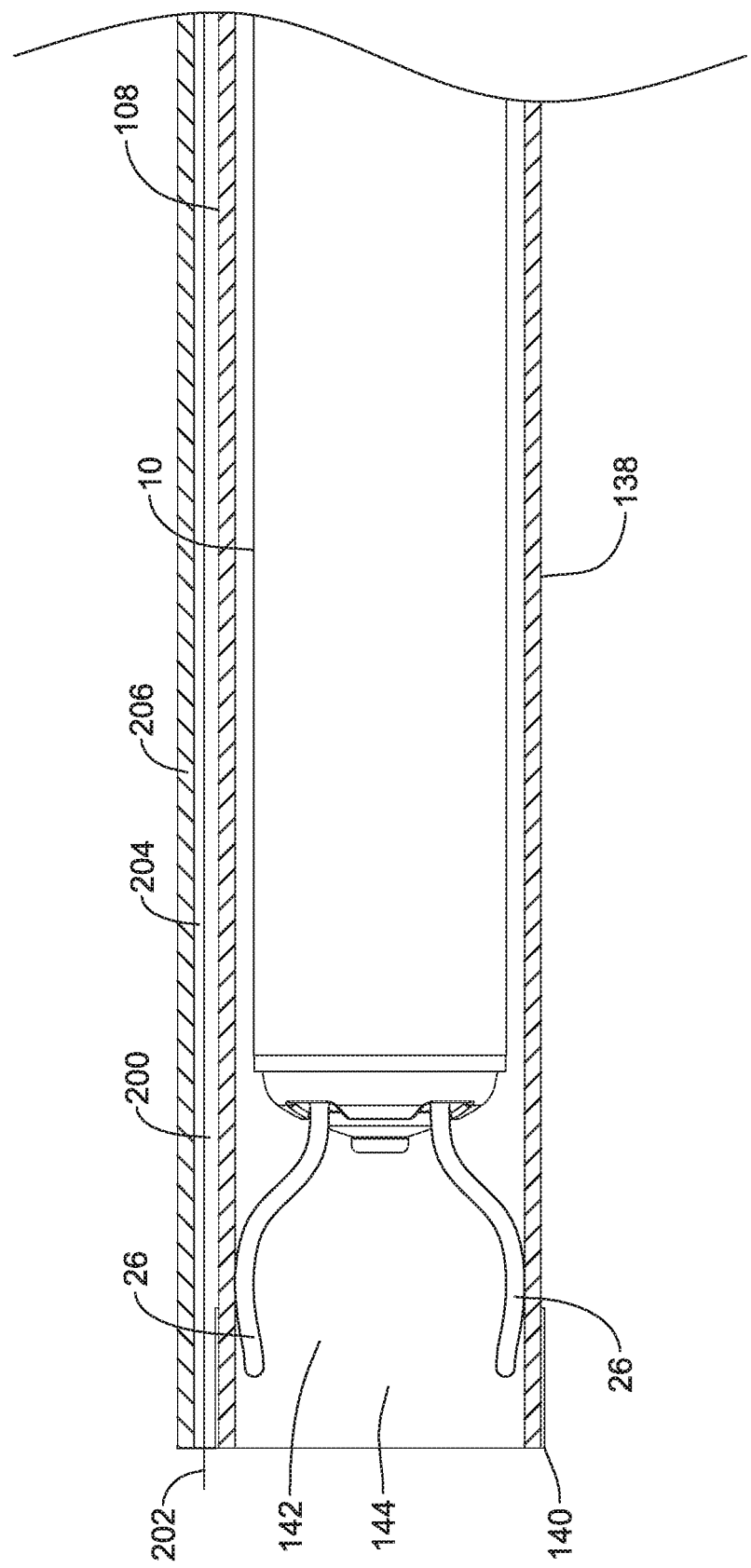
FIG. 7 is a partial cross-sectional side view of another illustrative distal portion of the delivery device of FIG. 4.

Once the distal tip portion 140 of the distal holding section 108 has been positioned adjacent to the cardiac tissue where the device 10 is desired, the distal holding section 108 may be temporarily anchored to the septal wall S. It is contemplated that the anchor may be a passive anchor or an active anchor, as desired. An active anchor 190 may actuated such that it penetrates into the septal wall S, as shown in FIG. 6D. A passive anchor may include the distal tip portion 140 of the distal holding section 108 resting on or engaging a structure of the heart such as, but not limited to a base of a papillary muscle, a moderator band, trabeculae, etc., as will be described in more detail with respect to FIG. 8. The active anchor 190 may be a manually actuated mechanism that may be deployed from the distal holding section 108 to anchor the distal tip portion 140 of the distal holding section 108 to the cardiac tissue. For example, the active anchor 190 may include a projection or penetrator configured to be actuated relative to the distal tip portion 140 of the distal holding section 108 to penetrate into the septal wall S or otherwise engage tissue. Referring briefly to FIG. 7 which illustrates a partial cross-section of the distal holding section 108 including an active anchor element, in some cases, the active anchor element may be a manually actuated atraumatic fixation mechanism or wire 200. The active anchor, such as wire 200, may include a fixation spike or distal tip 202 configured to engage a tissue and penetrate into the septal wall S upon actuation relative to the distal holding section 108. In some cases, the distal tip 202 may be formed as a unitary structure with the wire 200. In other cases, the distal tip 202 may be formed as a separate component from the wire 200 and fixedly coupled thereto. Thereby, actuation of the wire 200 may deploy the distal tip 202 to penetrate into the septal wall S.

The wire 200 may be slidably disposed within a lumen 204. It is contemplated that the lumen 204 may be formed by an additional sidewall 206 formed in addition to the body portion 138 of the distal holding section 108. Alternatively, the lumen 204 may be formed within the body portion 138 of the distal holding section 108. In other cases, the wire 200 and/or the lumen 204 may be positioned within the cavity 142 of the distal holding section 108. It is further contemplated that the wire 200 may not be disposed within a separate lumen, such as lumen 204. For example, the wire 200 may be slidably disposed along an inner or outer surface of the body portion 138 of the distal holding section 108. It is further contemplated that the wire 200 may be disposed within and/or on other components of the delivery system 100, as desired.

The wire 200 may be coupled to an actuation mechanism, for example, at the handle assembly, such that the wire 200 can be manually actuated between a retracted delivery configuration and an extended fixation configuration. The actuation mechanism may be a thumb slide, a dial, a button, etc. Distal movement or advancement of the wire 200 may cause the distal tip 202 of the wire 200 to extending distally beyond the distal tip portion 140 of the distal holding section 108. Proximal movement or retraction of the wire 200 may cause the distal tip 202 to retract proximally such that the distal tip 202 is adjacent to or proximal to the distal tip portion 140 of the distal holding section 108. It is contemplated that the distal tip 202 of the wire 200 may be in the range of 0.5 millimeters to 2.5 millimeters in length and 0.5 to 1.0 millimeters in diameter. In some cases, the distal tip 202 of the wire 200 may be configured to extend 0.5 millimeters to 2.5 millimeters beyond the distal tip portion 140 of the distal holding section 108 when the wire 200 is in an extended or advanced configuration.

Deployment or actuation of the active anchor relative to the distal holding section 108, may anchor the distal tip portion 140 to the septal wall S at one circumferential point about the distal tip portion 140. In the case of a passive anchor, the passive anchor may anchor the distal tip portion 140 to the septal wall S at one circumferential point about the distal tip portion 140.

Figure 6E:
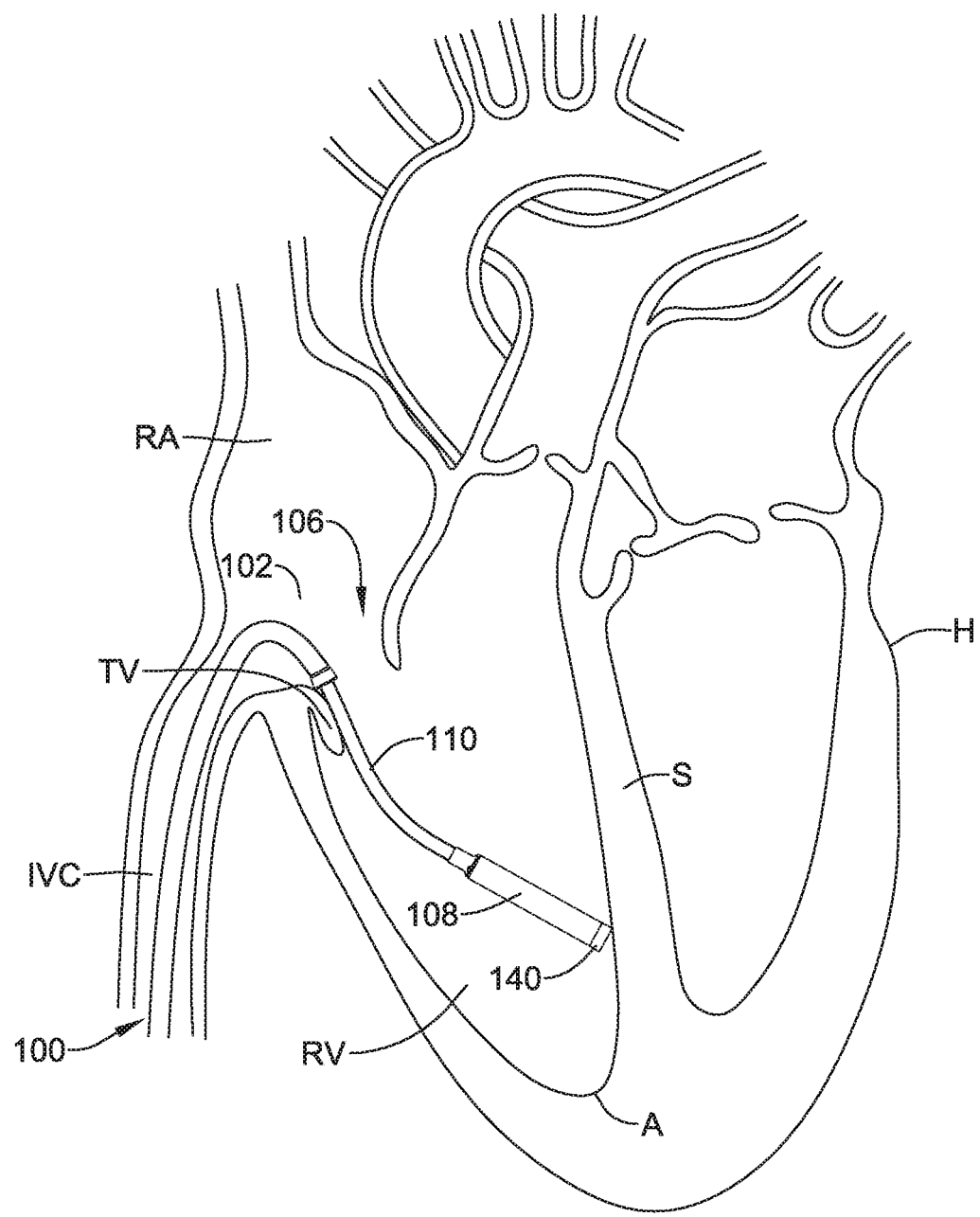

Once the distal tip portion 140 of the distal holding section 108 has been positioned adjacent to the cardiac tissue where the device 10 is desired and the distal tip portion 140 is temporarily anchored, the distal holding section 108 may be steered such that the opening 144 is pointed towards or generally towards the septum, as shown in FIG. 6E. For example, the handle assembly 120 (e.g., the first hub portion 126) may be torqued or rotated in a second direction opposite to the first direction (e.g. in a counter-clockwise direction) such that the distal holding section 108 tils relative to the septal wall S and the angle A between the longitudinal axis 182 of the distal holding section 108 and the septal wall S increases. For instance, the handle assembly 120 (e.g., the first hub portion 126) may be torqued or rotated in a second direction opposite to the first direction (e.g. in a counter-clockwise direction) such that the angle A between the longitudinal axis 182 of the distal holding section 108 is in the range of 5° to 90°, 10° to 85°, 15° to 85°, 15° to 75°, 30° to 75°, or 5° to 45° to the septum S. Such an increase in the angle A may enhance the apposition of the distal tip portion 140 with the septum S. However, while a greater angle may provide more direct contact of the distal tip portion 140 with the septum S, such rotation may be limited by the size (e.g., width) of the right ventricle. In some cases, the outer tubular member 102 may be torqued counter-clockwise while the intermediate tubular member 110 is within the right ventricle. It is contemplated that an excess of intermediate tubular member 110 within the right ventricle in combination with the anchored distal tip portion 140 may cause the opening 144 of the distal holding section 108 to tilt towards the septum S, as shown in FIG. 6E.

As described above, the intermediate tubular member 110 may include one or more actuation or deflection mechanism(s) that may allow for the intermediate tubular member 110, or portions thereof, to be deflected, articulated, steered and/or controlled in a desired manner. Such a deflection mechanism may be controlled at the handle assembly 120 to deflect the distal holding section 108 toward the septum S or in a superior and/or inferior direction, as desired. In some embodiments, the intermediate tubular member 110 may include a fixed or preformed curve along any portion of the length thereof to facilitate placement of the device. A fixed or preformed curve may be enhanced or reinforced by one or more nitinol wires embedded in the body of the intermediate tubular member to help preserve the preformed shape. In some cases, the nitinol wire may be formed such that the nitinol wire assumes the curved preformed shape at body temperature, although this is not required. In some cases, the preformed curve may be biased into a generally straightened configuration by the outer tubular member 102. The intermediate tubular member 110 may assume the preformed curved configuration as it is telescoped or distally advanced from the outer tubular member 102. It is contemplated that the intermediate tubular member 110 may include both a deflection mechanism and a preformed curve. The deflection mechanism and/or preformed curve, when provided individually or together maybe formed such that the curves occur in a different plane than the outer tubular member 102. Providing mechanisms that allow the delivery assembly 100 to be curved or deflected in more than one plane may facilitate steering the device 10 towards the septum S.

Figure 6F:
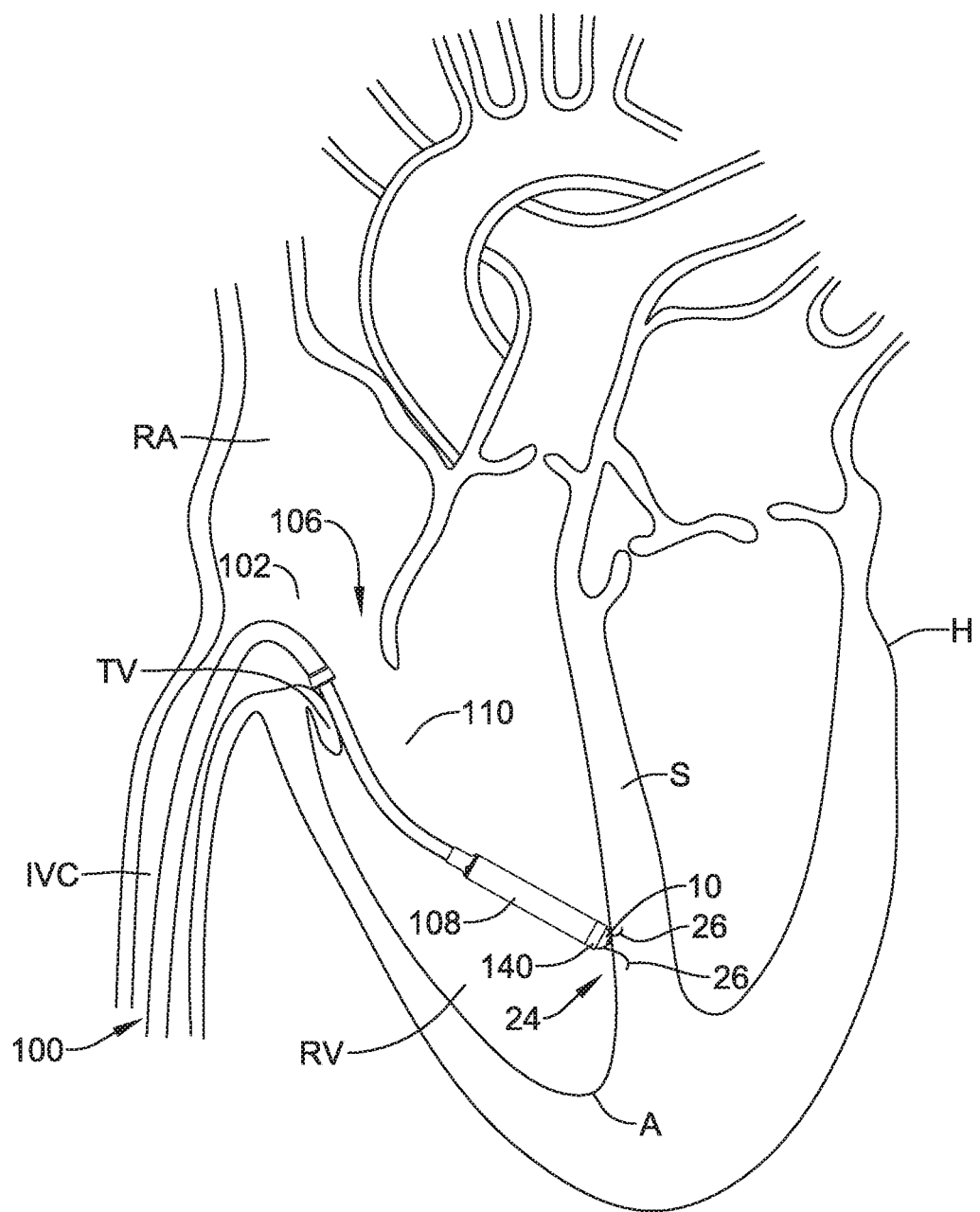
Figure 6G:
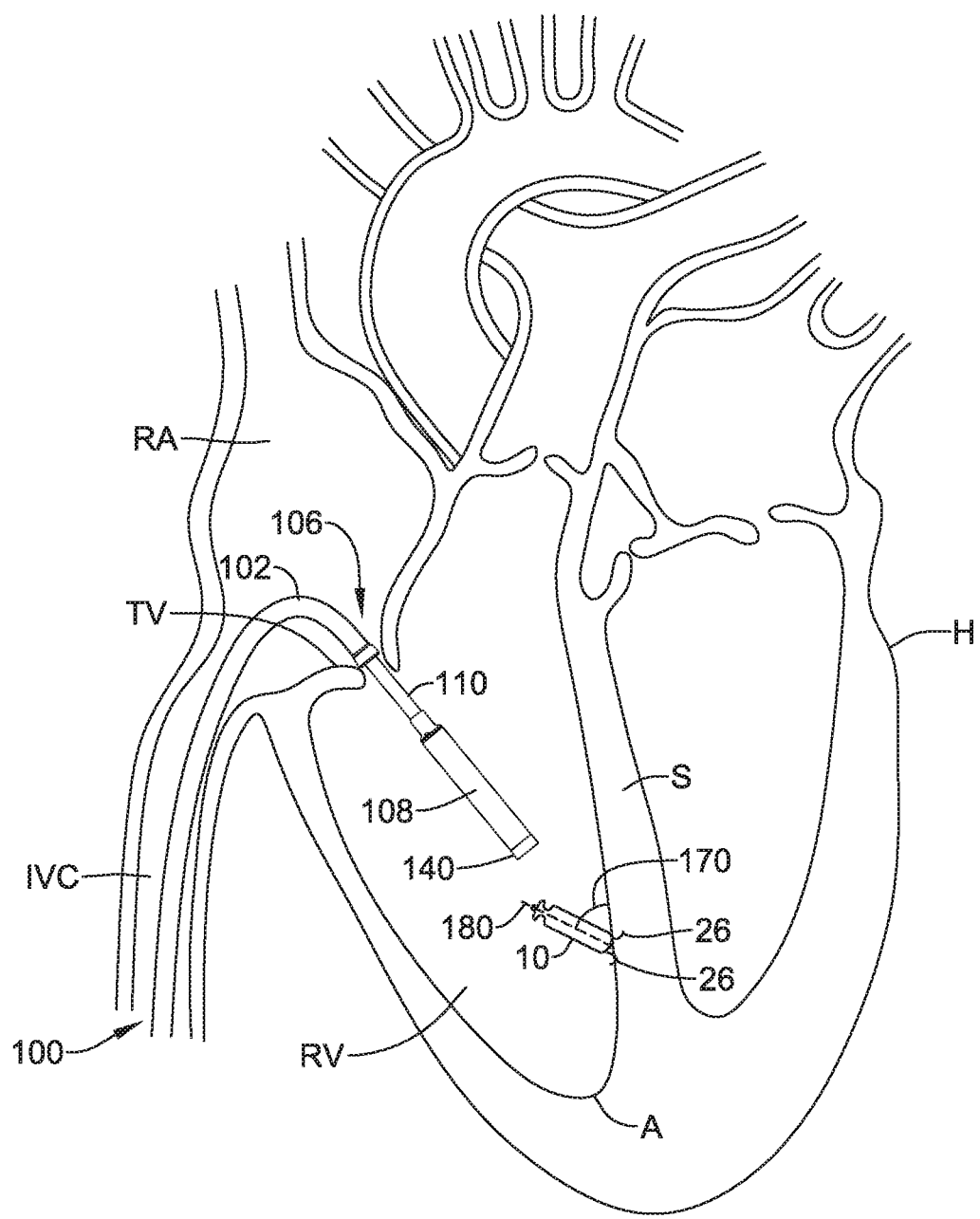

Once the distal tip portion 140 of the distal holding section 108 has been positioned adjacent to the cardiac tissue where the device 10 is desired, deployment of the device 10 can begin. It is contemplated that the location of the distal tip portion 140 may be confirmed with contrast media and imaging. The first stage of the deployment of the device 10 may enable activation of the fixation mechanism 24. The device 10 may be distally advanced out of the distal holding section 108 to deploy the hooks or tines 26 from the distal holding section 108 to engage the hooks or tines 26 in the heart tissue while the proximal portion of the device 10 remains within the distal holding section 108, as shown in FIG. 6F. In some embodiments, the location and/or fixation of the device 10 may be confirmed with contrast media, although this is not required. The second stage of the deployment of the device 10 may proximally retract the distal holding section 108, and thus the intermediate tubular member 110, relative to the inner tubular member 116 to fully deploy the device 10, as shown in FIG. 6G. The temporary passive or active fixation of the distal holding section 108 may be released after the first or second stage of deployment of the device 10, as desired. The device 10 may be deployed such that a longitudinal axis 180 of the device 10 is at an angle 170 in the range of approximately 5° to 90°, 15° to 75°, 30° to 60°, or in the range of 5° to about 45° to the septum S. Once the clinician has determined that the position of the device 10 is satisfactory and the fixation mechanism 24 is securely engaged with the heart tissue, the intermediate tubular member 110, including the distal holding section 108, of the delivery device 100 can be proximally retracted.

Figure 8:
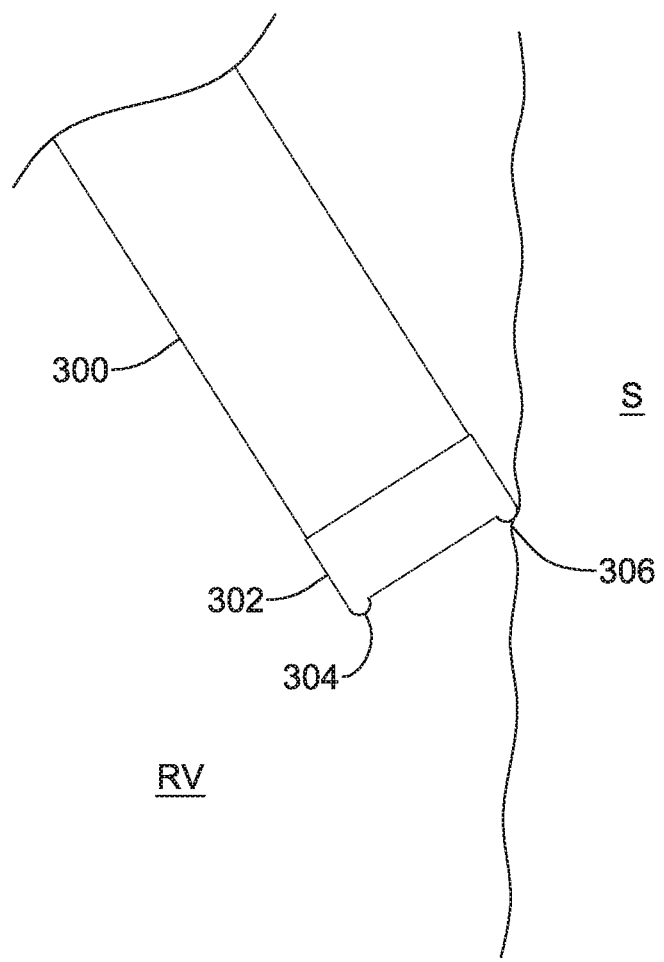
FIG. 8 is a close up view of an illustrative implantable leadless cardiac pacing device passively anchoring to a septal wall.

FIG. 8 illustrates a passive anchoring of an illustrative distal holding section 300 to the septum S. The distal holding section 300 may be similar in form and function to the distal holding section 108 described herein and may similarly be affixed at a distal end of a delivery system. The distal holding section 300 may include a distal tip portion 302 similar in form and function to the distal holding section 140 described herein. The distal tip portion 302 may include an annular rim 304, which in some instances may include one or more protrusions or other bumps, grooves, or textured surface configured to engage the septum. The annular rim 304 may be configured to passively engage (e.g., rest upon) a structure 306 of the heart such as, but not limited to a base of a papillary muscle, a moderator band, trabeculae, etc. This may provide a mechanical stop without activation of any additional structure or penetration of the septum S. It is contemplated that the distal holding section 300 may be free from any structure (e.g., annular rim 304) configured to engage the heart tissue.

It is contemplated that delivering the device 10 to the septum S allows the device 10 to be deployed in a thicker part of the right ventricle RV which may reduce the risk of cardiac perforation. It is further contemplated that placing the pacing electrode 20 in contact with the septum S instead of the apex A may provide superior pacing. The ability to move the intermediate tubular member 110 independent of the outer tubular member 102 may also provide greater flexibility in maneuvering the distal holding section 108 in different directions (e.g., left, right, inferior, superior, etc.) which may allow the clinician more control in the placement location of the device 10. For example, the present delivery device and method for delivering the device 10 may allow a clinician more consideration of the physiological characteristics of the placement location as more locations are accessible (e.g., infarcted tissue can be more readily avoided as a placement location).

While a method has been described in which the device 10 is delivered to the right ventricular septum, it is contemplated that a similar method may be used to deliver the device 10 to the lateral free wall of the left ventricle. For example, instead of deploying the device 10 to the septum S, the distal holding section 108 may be advanced through a puncture or hole in the septum S, sometimes through a transatrial septal puncture. It is contemplated that the distal holding section 108 may be guided to the septum in a similar manner as described above using temporary fixation of the distal holding section 108 and manipulation of the handle assembly 120 to guide the distal holding section 108 through and/or to form the puncture.

The materials that can be used for the various components of the delivery devices, such as delivery device 100 (and/or other delivery structures disclosed herein) and the various members disclosed herein may include those commonly associated with medical devices. For simplicity purposes, the following discussion makes reference the delivery device 100, and components of thereof. However, this is not intended to limit the devices and methods described herein, as the discussion may be applied to other similar delivery systems and/or components of delivery systems or devices disclosed herein.

The delivery device 100 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY®

ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of delivering an implantable leadless pacing device to a ventricular septum, the method comprising:
    advancing a delivery device through the vasculature and into the right atrium, the delivery device comprising:
        an outer tubular member including a lumen extending from a proximal end to a distal end thereof, the outer tubular member configured to be deflectable in a first a plane;
        an intermediate tubular member including a lumen extending from a proximal end to a distal end thereof, the intermediate tubular member slidably disposed within the lumen of the outer tubular member, the intermediate tubular member including a distal holding section defining a cavity therein for receiving an implantable leadless pacing device, and the intermediate tubular member configured to be deflectable in a second plane different from the first plane;
        an inner tubular member including a lumen extending from a proximal end to a distal end thereof, the inner tubular member slidably disposed within the lumen of the intermediate tubular member;
        a handle assembly including at least a first hub portion affixed adjacent to the proximal end of the outer tubular member, a second hub portion affixed adjacent to the proximal end of the intermediate tubular member, and a third hub portion affixed adjacent to the proximal end of the inner tubular member; and
        a first actuation mechanism positioned at the handle assembly and configured to deflect the outer tubular member;
    distally advancing the intermediate tubular member across the tricuspid valve and into the right ventricle;
    torquing the outer tubular member in a first direction to guide the distal holding section along the ventricular septum;
    releaseably securing a distal tip of the distal holding section to a tissue in the ventricular septum;
    after securing the distal tip of the distal holding section, torqueing the outer tubular member in a second direction opposite to the first direction; and
    incrementally deploying an implantable leadless pacing device.

2. The method of claim 1, wherein the implantable leadless pacing device is deployed such that a longitudinal axis of the implantable leadless pacing device is at an angle of in the range of 5 to 45° to the ventricular septum.

3. The method of claim 1, wherein releaseably securing the distal tip of the distal holding section to the tissue comprises a passive anchoring of the distal tip to the ventricular septum.

4. The method of claim 1, wherein releaseably securing the distal tip of the distal holding section to the tissue comprises an active anchoring of an active anchoring element to the ventricular septum.

5. The method of claim 1, further comprising unsecuring the distal tip of the distal holding section from the tissue after the implantable leadless pacing device has been at least partially deployed.

6. The method of claim 1, wherein torquing the outer tubular member in the first direction comprises deflecting the outer tubular member in the first plane.

7. The method of claim 1, wherein torquing the outer tubular member in the second direction opposite to the first direction orients an opening of the distal holding section towards the ventricular septum.

8. A method of delivering an implantable leadless pacing device to a ventricular septum, the method comprising:
    advancing a delivery device through the vasculature and into the right atrium, the delivery device comprising:
        an outer tubular member including a lumen extending from a proximal end to a distal end thereof;
        an intermediate tubular member including a lumen extending from a proximal end to a distal end thereof, the intermediate tubular member slidably disposed within the lumen of the outer tubular member, the intermediate tubular member including a distal holding section defining a cavity therein for receiving an implantable leadless pacing device;
        an inner tubular member including a lumen extending from a proximal end to a distal end thereof, the inner tubular member slidably disposed within the lumen of the intermediate tubular member;
        a handle assembly including at least a first hub portion affixed adjacent to the proximal end of the outer tubular member, a second hub portion affixed adjacent to the proximal end of the intermediate tubular member, and a third hub portion affixed adjacent to the proximal end of the inner tubular member; and
        a first actuation mechanism positioned at the handle assembly and configured to deflect the outer tubular member;
    distally advancing the intermediate tubular member across the tricuspid valve and into the right ventricle;
    torquing the outer tubular member in a first direction to guide the distal holding section along the ventricular septum by rotating the first hub portion in the first direction;
    releaseably securing a distal tip of the distal holding section to a tissue in the ventricular septum;

after securing the distal tip of the distal holding section, torquing the outer tubular member in a second direction opposite to the first direction by rotating the first hub portion in the second direction; and deploying an implantable leadless pacing device from the distal holding section.

9. The method of claim 8, wherein the implantable leadless pacing device is deployed such that a longitudinal axis of the implantable leadless pacing device is at an angle of in the range of 5 to 45° to the ventricular septum.

10. The method of claim 8, wherein releaseably securing the distal tip of the distal holding section to the tissue comprises a passive anchoring of the distal tip to the ventricular septum.

11. The method of claim 8, wherein releaseably securing the distal tip of the distal holding section to the tissue comprises an active anchoring of an active anchoring element to the ventricular septum.

* * * * *